(12) United States Patent  
Wakita

(10) Patent No.: US 7,915,439 B2  
(45) Date of Patent: Mar. 29, 2011

(54) METHOD OF PRODUCING SILYLALKOXYMETHYL HALIDE

(75) Inventor: Keiji Wakita, Ichihara (JP)

(73) Assignee: Dow Corning Toray Company, Ltd., Tokyo (JP)

( * ) Notice: Subject to any disclaimer, the term of this patent is extended or adjusted under 35 U.S.C. 154(b) by 228 days.

(21) Appl. No.: 11/577,047

(22) PCT Filed: Sep. 28, 2005

(86) PCT No.: PCT/JP2005/018405  
§ 371 (c)(1),  
(2), (4) Date: Apr. 27, 2009

(87) PCT Pub. No.: WO2006/040964  
PCT Pub. Date: Apr. 20, 2006

(65) Prior Publication Data  
US 2009/0203932 A1 Aug. 13, 2009

(30) Foreign Application Priority Data  
Oct. 13, 2004 (JP) ................... 2004-298875

(51) Int. Cl.  
*C07F 7/08* (2006.01)  
*C07F 7/04* (2006.01)
(52) U.S. Cl. ..................................... 556/449
(58) Field of Classification Search .......... None  
See application file for complete search history.

(56) References Cited

U.S. PATENT DOCUMENTS

| | | | |
|---|---|---|---|
| 5,618,631 | A | 4/1997 | Meguriya et al. |
| 5,645,941 | A | 7/1997 | Meguriya et al. |
| 5,714,265 | A | 2/1998 | Meguriya et al. |
| 5,859,127 | A | 1/1999 | Nakano et al. |
| 6,235,862 | B1 | 5/2001 | Isshiki et al. |
| 7,074,936 | B2 * | 7/2006 | Caprioli et al. ............ 546/339 |
| 2002/0028335 | A1 | 3/2002 | Fujiki et al. |
| 2003/0212230 | A1 | 11/2003 | Rubinsztajn et al. |

FOREIGN PATENT DOCUMENTS

| | | |
|---|---|---|
| EP | 0464706 A1 | 1/1992 |
| EP | 0543384 A1 | 5/1993 |
| EP | 0567079 A1 | 10/1993 |
| EP | 0571965 A1 | 12/1993 |
| EP | 0620242 A2 | 10/1994 |
| EP | 0821038 A2 | 1/1998 |
| EP | 1002834 A1 | 5/2000 |
| GB | 2 279 616 A | 1/1995 |
| JP | 5295084 | 11/1993 |
| JP | 06-306084 | 11/1994 |
| JP | 7-022441 | 1/1995 |
| JP | 7-118365 | 5/1995 |
| JP | 07-161740 | 6/1995 |
| JP | 08-176447 | 7/1996 |
| JP | 09-095651 | 4/1997 |
| JP | 10-130465 | 5/1998 |
| JP | 10-147764 | 6/1998 |
| JP | 10-163232 | 6/1998 |
| JP | 11012546 | 1/1999 |
| JP | 2004-043814 | 2/2004 |
| JP | 2004-043815 | 2/2004 |
| WO | WO 02/097393 A3 | 12/2002 |
| WO | WO 2005/021652 A1 | 3/2005 |
| WO | WO 2005/044920 A1 | 5/2005 |

OTHER PUBLICATIONS

Pyne et al., {Chiral and stereochemical control via intramolecular Diels-Alder reaction of Z dienes, Journal of the American Chemical Society (1982), 104(21), 5719-5728}.*  
Shipov et al., {Synthesis of alkyl chloromethyl ethers, Journal of General Chemistry of the USSR, vol. 59, No. 5.2, 1989, p. 1067}.*  
English language abstract for JP5295084 extracted from esp@cenet.com, Jan. 11, 2007.  
English language translation and abstract for JP06-306084 extracted from Searching PAJ, Jan. 1, 2008, pp. 28.  
English language translation and abstract for JP07-022441 extracted from Searching PAJ, Jan. 1, 2008, pp. 15.  
English language translation and abstract for JP07-118365 extracted from Searching PAJ, Jan. 1, 2008, pp. 16.  
English language translation and abstract for JP07-161740 extracted from Searching PAJ, Jan. 1, 2008, pp. 15.  
English language translation and abstract for JP08-176447 extracted from Searching PAJ, Dec. 9, 2007, pp. 28.  
English language translation and abstract for JP09-095651 extracted from Searching PAJ, Jan. 1, 2008, pp. 15.  
English language translation and abstract for JP10-130465 extracted from Searching PAJ, Jan. 1, 2008, pp. 12.  
English language translation and abstract for JP10-147764 extracted from Searching PAJ, Jan. 1, 2008, pp. 14.  
English language translation and abstract for JP10-163232 extracted from Searching PAJ, Jan. 1, 2008, pp. 16.  
English language abstract for JP11-012546 extracted from esp@cenet.com, Dec. 16, 2007.  
English language translation and abstract for JP2004-043814 extracted from Searching PAJ, Dec. 16, 2007, pp. 51.  
English language translation and abstract for JP2004-043815 extracted from Searching PAJ, Dec. 9, 2007, pp. 21.  
PCT International Search Report for PCT/JP2005/011864, Nov. 10, 2005, 5 pages.  
PCT International Search Report for PCT/JP2005/024196, Mar. 8, 2006, 3 pages.  
PCT International Search Report for PCT/JP2006/303996, Jul. 7, 2006, 3 pages.

(Continued)

*Primary Examiner* — Daniel M Sullivan  
*Assistant Examiner* — Chukwuma O Nwaonicha  
(74) *Attorney, Agent, or Firm* — Howard & Howard Attorneys PLLC

(57) ABSTRACT

A method for making a silylalkoxymethyl halide at good yield represented by the formula:

$$R^1R^2R^3Si-R^4-O-CH_2X$$

wherein $R^1$, $R^2$, and $R^3$ are an alkyl, cycloalkyl, aryl group, or a halogen atom, $R^4$ is a divalent hydrocarbyl group having 1 to 10 carbon atoms, and X is a halogen atom, by reacting:  
(a) a silyl alcohol compound with the formula $R^1R^2R^3Si-R^4-OH$ wherein $R^1$, $R^2$, $R^3$ and $R^4$ are defined as above, with  
(b) formaldehyde or a polymer thereof, and  
(c) a halosilane.

8 Claims, No Drawings

OTHER PUBLICATIONS

PCT International Search Report for PCT/JP2006/309218, Jul. 14, 2006, 4 pages.

PCT International Search Report for PCT/JP2006/039219, Aug. 18, 2006, 4 pages.

Yongxin Han et al. "Silicon Directed ipso-Substitution of Polymer Bound Arylsilanes: Preparation of Biaryls via", Tetrahedron Letters, vol. 37, No. 16. 1996, pp. 2703-2706.

Schultz et al., "The Synthesis Of Trimethylsilylmethoxymethyl Chloride", OPPI Briefs, vol. 27, No. 5, 1995, pp. 572-574.

Hojo et al., "New Access to Carbonyl Ylides by the Silicon-Based 1,3-Elimination and Their:..", Tetrahedron Letters, vol. 34, No. 37, 1993, pp. 5943-5946.

Boons et al., "Use of (Phenyldimethylsilyl)methoxymethyl and (Phenyldimethylsilyl) methyl ethers . . . ", Tetrahedron Letters, vol. 31, No. 15, 1990, pp. 2197-2200.

Hasseberg et al., "104. Synthese von Orellin", Helvetica Chimica Acta—vol. 71, No. 5, 1988, pp. 957-963.

Guedin-Vuong et al., "An Easy Access to Homopropargylic Ethers", Bulletin De La Societe Chimique De France, No. 2, 1986, pp. 245-252.

Pyne et al., "Chiral and Stereochemical Control via Intramolecular Diels-Alder Reaction of Z Dienes", J. American Chemical Society, vol. 104, No. 21, 1982, pp. 5719-5728.

Lipshutz et al., "B-(Trimethylylsilyl) Ethoxymethyl Chloride . . . , " Tetrahedron Letters, vol. 21, No. 35, 1980, pp. 3343-3346.

Shikhiev et al., "Synthesis and Reactions of Unsaturated Organosilicon Compounds", J. Of General Chemistry of the USSR, vol. 41, No. 3, 1971, pp. 617-619.

Shipov et al., "Synthesis of Alkyl Chloromethyl Ethers", J. Of General Chemistry of the USSR, vol. 59, No. 5.2, 1989, p. 1067.

Miramon et al., "Short Synthesis of Polyoxygenated Macrocyclic . . . ", Journal of Organic Chemistry, vol. 69, No. 20, 2004, pp. 6949-6952.

Shikhiev et al., "Synthesis and Reactions of Some Heteroorganic Ethers . . . ", J. Of General Chemistry of the USSR, vol. 45, No. 1, 1975, pp. 91-93.

* cited by examiner

METHOD OF PRODUCING SILYLALKOXYMETHYL HALIDE

RELATED APPLICATIONS

This application claims priority to and all the advantages of International Patent Application No. PCT/JP2005/018405, filed on Sep. 28, 2005, which claims priority to Japanese Patent Application No. JP2004-298875, filed on Oct. 13, 2004.

FIELD OF THE INVENTION

This invention relates to a novel method of manufacturing a silylalkoxymethyl halide, the product being obtained easily and with a high yield.

BACKGROUND OF THE INVENTION

Silylalkoxymethyl halides are publicly known. Among these compounds, trimethylsilylmethoxymethyl chloride and phenyldimethylsilylmethoxymethyl chloride in particular are very important in the synthesis of bio-active substances and natural products with complex structures as reagents that protect functional groups containing active hydrogen.

Some examples of synthesis by several methods have already been reported for silylalkoxymethyl chlorides such as trimethylsilylmethoxymethyl chloride and phenyldimethylsilylmethoxymethyl chloride (See to Bruce H. Lipshutz et al., Tetrahedron Letters (Great Britain), Volume 21 (1980), pp. 3343-3346; Denis Guedin-Vunong et al., Bulletin de la Societe Chimique de France (France), No. 2 (1986), pp. 245-252; Arthur G. Schultz et al., Organic Preparations and Procedures International (US), Volume 27 (1995), pp. 572-574; and G. J. P. H. Boons et al., Tetrahedron Letters (Great Britain), Volume 31 (1990), pp. 2197-2200). These synthesis examples involve chloromethylation of the corresponding silyl alcohol using hydrogen chloride gas in the presence of a formaldehyde polymer.

However, there is a substantial problem to execute this procedure on an industrial basis. Specifically, the generation of by-product water cannot be avoided during chloromethylation using hydrogen chloride gas, and this water reacts with the product, resulting in product decomposition. The result is either a major reduction in the yield of the target silylalkoxymethyl chloride or a complete failure to obtain the target silylalkoxymethyl chloride.

In the aforementioned references, the by-product water is removed from the system by introducing a dehydrating agent, such as magnesium sulfate, immediately after the reaction. However, the implementation of this procedure on an industrial basis is cumbersome and complicated, and the product decomposition also proceeds during the time required to carry out the dehydration treatment. Moreover, the dehydrating agent must be separated from the product by, for example, filtration, which lengthens the process time, increases the amount of waste, raises the production costs, and lowers the yield.

In addition to the preceding, hydrogen chloride gas is a gaseous reagent and thus is much more difficult to handle than ordinary liquid reagents. It is difficult, in particular, to measure the amount used in the reaction, making it necessary to use a large excess of the gas and thereby raising the costs and increasing the amount of waste.

A. G. Shipov et al., Zhumal Obshchei Khimii (formerly the USSR), Volume 59 (1989), pp. 1204-1205, describes a method for manufacturing alkoxymethyl chloride by the reaction of an aryl alcohol or alkyl alcohol with formula (3)

R—OH    (3)

wherein R is phenylmethyl or an alkyl group having 1, 5, 8, 10 or 12 carbon atoms, with paraformaldehyde in chlorotrimethylsilane. However, this reference does neither describe nor suggest the use of a silyl alcohol as a starting material.

SUMMARY OF THE INVENTION

This invention solves the problems noted above, and its object is the introduction of a high yield method of manufacturing silylalkoxymethyl halide. The method does not require the use of difficult-to-handle hydrogen chloride gas, it does not generate by-product water, it does not require a dehydrating agent, it generates little solid waste, and it requires less time for manufacturing silylalkoxymethyl halide than current methods.

As a result, in accordance with the invention, it has been discovered that a silylalkoxymethyl halide represented by formula (1):

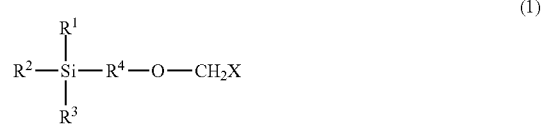

wherein $R^1$, $R^2$, and $R^3$ are alkyl, cycloalkyl, aryl group, or a halogen atom, $R^4$ is divalent hydrocarbyl group having 1 to 10 carbon atoms, and X is a halogen atom, could be synthesized at good efficiencies by reacting (a) a silyl alcohol compound represented by formula (2):

wherein $R^1$, $R^2$, and $R^3$ are alkyl, cycloalkyl, aryl, or a halogen atom, and $R^4$ is divalent hydrocarbyl group having 1 to 10 carbon atoms, with (b) formaldehyde or a polymer thereof, and (c) a halosilane.

It was also discovered that high purity silylalkoxymethyl halide could be obtained in high yields by distilling out, under the application of reduced pressure, hydrogen halide generated as a by-product in the reaction, excess halosilane, and the reaction product of water and halosilane; and thereafter adding (d) a tertiary amine, and distilling the silylalkoxymethyl halide.

The method of the invention enables a high yield and industrially facile and efficient synthesis of a silylalkoxymethyl halide represented by formula (1):

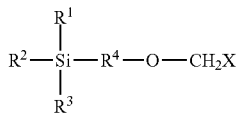

(1)

wherein $R^1$, $R^2$, and $R^3$ are alkyl, cycloalkyl, aryl, or a halogen atom, $R^4$ is divalent hydrocarbyl group having 1 to 10 carbon atoms, and X is a halogen atom, without using either hydrogen chloride gas or a dehydrating agent, and it does so while making it possible to reduce the amount of solid waste.

DETAILED DESCRIPTION OF THE INVENTION

According to the method, the (a) silyl alcohol compound represented by formula (2):

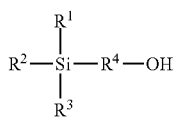

(2)

is the primary starting material. $R^1$, $R^2$, and $R^3$ in formula (2) are alkyl, cycloalkyl, aryl, or a halogen atom, while $R^4$ is a divalent hydrocarbyl group having 1 to 10 carbon atoms. $R^1$, $R^2$, and $R^3$ can be specifically exemplified by alkyl groups such as methyl, ethyl, propyl, isopropyl, butyl, isobutyl, pentyl, isopentyl, hexyl, and isohexyl; cycloalkyl groups such as cyclopentyl, cyclohexyl, and cycloheptyl; aryl groups such as phenyl, tolyl, xylyl, and naphthyl; and halogen atoms such as the chlorine atom and fluorine atom. $R^4$ is specifically exemplified by methylene; alkylene having 2 to 10 carbon atoms such as ethylene, propylene, and butylene; cycloalkylene having 3 to 10 carbon atoms such as cyclopentylene and cyclohexylene; and arylene having 6 to 10 carbon atoms such as phenylene and naphthylene. When the compound represented by formula (1) prepared in accordance with the invention is used as a reagent for protecting active hydrogen-containing functional groups, $R^1$, $R^2$, and $R^3$ are preferably methyl, ethyl, propyl, isopropyl, or phenyl, and $R^4$ preferably is methylene, ethylene, or propylene, and more preferably ethylene. The silyl alcohol compound represented by formula (2) can be specifically exemplified by trimethylsilylmethanol, 2-trimethylsilylethanol, 3-trimethylsilylpropanol, 2-triethylsilylethanol, 2-triisopropylsilylethanol, and 2-dimethylphenylsilylethanol. These silyl alcohol compounds can in some cases be acquired as reagents, and when necessary can also be synthesized by known procedures.

The (b) formaldehyde or polymer thereof is a generally known formaldehyde equivalent. Usable here are, inter alia, gaseous formaldehyde, trioxane (the trimer), and paraformaldehyde (a polymer). Granular paraformaldehyde is particularly preferred from the standpoints of reactivity and ease of handling. Aqueous formalin solutions are undesirable due to the negative effects exercised by their water fraction. The formaldehyde or polymer thereof may be used in a small excess, and preferably in the range of 1 to 1.5 equivalents, with respect to the (a) silyl alcohol compound with formula (2).

The (c) halosilane functions to react with the silyl alcohol compound and thereby produces the hydrogen halide required by the halomethylation reaction, and at the same time functions to scavenge the water generated as a by-product. When the compound represented by formula (1) prepared in accordance with the invention is used as a reagent for protecting active hydrogen-containing functional groups, the halosilane is preferably a chlorosilane or a bromosilane, and more preferably is a chlorosilane. Specific examples are tetrachlorosilane, methyltrichlorosilane, chlorotrimethylsilane, and chlorotriethylsilane. Chlorotrimethylsilane is most preferred when one considers its ease of acquisition and ease of separation of the product after water scavenging. The (c) halosilane is desirably used in excess relative to the (a) silyl alcohol compound represented by formula (2), wherein 2 to 20 equivalents is preferred, and 3 to 5 equivalents is more preferred, in each case referred to the (a) silyl alcohol compound represented by formula (2).

The reaction among the (a) silyl alcohol compound represented by formula (2), (b) formaldehyde or polymer thereof, and the (c) halosilane proceeds readily merely upon mixing the individual components. However, a procedure in which one component is added dropwise to a mixture of the other components is desirable, in order to avoid an overly vigorous reaction. More preferably, the reaction is appropriately carried out by adding the (a) silyl alcohol compound represented by formula (2) dropwise to a mixture of (b) formaldehyde or polymer thereof, and the (c) halosilane. The reaction temperature is preferably low, in order to avoid product decomposition and the range of 0 to 10° C. is most preferred. The reaction does not require solvent, but a solvent inert with respect to the individual components such as toluene, xylene, and heptane can be used when necessary.

The target material is obtained after the reaction by distilling out, under the application of reduced pressure, the hydrogen halide, excess halosilane, and water/halosilane reaction product. Purification by distillation is desirably carried out in order to provide an additional increase in target material purity. Improvements in the silylalkoxymethyl halide purity and reaction yield can be obtained by the addition of (d) tertiary amine to this distillative purification, in order to neutralize the hydrogen halide not completely distilled out under reduced pressure, and thereby more effectively inhibit product decomposition. This tertiary amine is preferably triethanolamine or diisopropylethylamine, and is more preferably diisopropylethylamine.

Silylalkoxymethyl halide represented by formula (1) prepared by the method in accordance with the invention can be exemplified by (trimethylsilyl)methoxyethyl chloride, 2-(trimethylsilyl)ethoxymethyl chloride, 3-(trimethylsilyl)propoxymethyl chloride, 2-(triethylsilyl)ethoxymethyl chloride, 2-(triisopropylsilyl)ethoxymethyl chloride, and 2-(dimethylphenylsilyl)ethoxymethyl chloride.

EXAMPLES

The invention is described by the examples provided below, but the invention is not limited to these examples. In these examples, the gas chromatograms and mass spectra of the reaction products were measured using a GCMS-QP5050A (Shimadzu Corporation). The reaction product was identified by agreement between the measurement results obtained for the reaction product using the GCMS-QP5050A, and the measurement results for a commercially acquired 2-(trimethylsilyl)ethoxymethyl chloride reference material (from Tokyo Kasei). The purity of the purified 2-(trimethylsilyl)ethoxymethyl chloride was calculated from the results of gas chromatographic measurement (GCMS-QP5050A) of the reference material and reaction product by comparing the respective peak area ratios.

Practical Example 1

13.5 g (0.45 mol) of paraformaldehyde and 125.0 g (1.15 mol) of chlorotrimethylsilane were introduced into a 300-mL four-neck flask fitted with a thermometer and stirrer. 54.4 g (0.46 mol) of 2-trimethylsilylethanol was added dropwise over 30 minutes while stirring and cooling with an ice bath. After warming the reaction mixture to room temperature, the pressure was reduced to 100 mmHg using an aspirator, and the hydrogen chloride was removed. The low boiling fraction was distilled off, and additional vacuum distillation was carried out to provide 34.0 g of 2-(trimethylsilyl)ethoxymethyl chloride. The 2-(trimethylsilyl)ethoxymethyl chloride product had a purity of 76%, and the yield was 33%.

Comparative Example 1

6.0 g (0.2 mol) of paraformaldehyde and 23.7 g (0.2 mol) of 2-trimethylsilylethanol were introduced into a 100-mL four-neck flask fitted with a thermometer and stirrer. Hydrogen chloride gas was bubbled in while stirring and cooling with an ice bath, but the end point of the reaction was unclear. While the production of 2-(trimethylsilyl)ethoxymethyl chloride while on the ice bath was confirmed, the 2-(trimethylsilyl)ethoxymethyl chloride produced underwent decomposition when the mixture was warmed to room temperature, and no target material whatever was obtained.

Practical Example 2

6.0 g (0.2 mol) of paraformaldehyde and 108.6 g (1 mol) of chlorotrimethylsilane were introduced into a 200-mL four-neck flask fitted with a thermometer and stirrer. 23.7 g (0.2 mol) of 2-trimethylsilylethanol was added dropwise over 30 minutes while stirring and cooling with an ice bath. After warming the reaction mixture to room temperature, the pressure was reduced to 100 mm Hg using an aspirator, and the hydrogen chloride was removed. After then adding 5 drops of diisopropylethylamine, the low boiling fraction was distilled off, and additional vacuum distillation was carried out to provide 22.9 g of 2-(trimethylsilyl)ethoxymethyl chloride. The purity of the obtained 2-(trimethylsilyl)ethoxymethyl chloride was very high, i.e., 98%, and the yield was 68%.

Practical Example 3

A reaction was carried out under the same conditions as in Practical Example 2, but using 36.1 g (0.2 mol) of 2-dimethylphenylsilylethanol in place of the 2-trimethylsilylethanol. 33.4 g of 2-(dimethylphenylsilyl)ethoxymethyl chloride was obtained. The purity of the 2-(trimethylsilyl)ethoxymethyl chloride was very high, i.e., 99%, and the yield was 73%.

INDUSTRIAL APPLICABILITY

The method in accordance with the invention is useful for the industrial production of silylalkoxymethyl halides such as trimethylsilylmethoxymethyl chloride and phenyldimethylsilylmethoxymethyl chloride.

The invention claimed is:

1. A method of manufacturing a silylalkoxymethyl halide of formula (1):

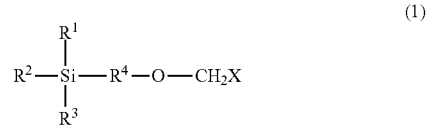

wherein $R^1$, $R^2$, and $R^3$ are an alkyl, cycloalkyl, aryl group, or a halogen atom, $R^4$ is a divalent hydrocarbyl group having 1 to 10 carbon atoms, and X is a halogen atom, comprising reacting:
(a) a silyl alcohol compound of formula (2):

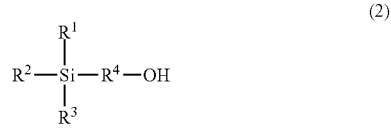

wherein $R^1$, $R^2$, and $R^3$ are an alkyl, cycloalkyl, aryl group, or a halogen atom, and $R^4$ is a divalent hydrocarbyl group having 1 to 10 carbon atoms, with
(b) formaldehyde or a polymer thereof, and
(c) a halosilane; and
distilling out, under reduced pressure, hydrogen halide generated as a by-product in the reaction, excess halosilane, and the reaction product of water and halosilane and thereafter adding (d) a tertiary amine.

2. The method according to claim 1 wherein the (a) silyl alcohol compound is trialkylsilylethanol, and the silylalkoxymethyl halide is trialkylsilylethoxymethyl halide.

3. The method according to claim 1 wherein the (c) halosilane is chlorotrialkylsilane, and the silylalkoxymethyl halide is silylalkoxymethyl chloride.

4. The method according to claim 1 further comprising purifying the silylalkoxymethyl halide by further distillation.

5. The method according to claim 1 wherein the (a) silyl alcohol compound is trialkylsilylethanol, and the silylalkoxymethyl halide is trialkylsilylethoxymethyl halide.

6. The method according to claim 4 wherein the (a) silyl alcohol compound is trialkylsilylethanol, and the silylalkoxymethyl halide is trialkylsilylethoxymethyl halide.

7. The method according to claim 1 wherein the (c) halosilane is chlorotrialkylsilane, and the silylalkoxymethyl halide is silylalkoxymethyl chloride.

8. The method according to claim 4 wherein the (c) halosilane is chlorotrialkylsilane, and the silylalkoxymethyl halide is silylalkoxymethyl chloride.

* * * * *